United States Patent
Bornzin et al.

(10) Patent No.: US 6,889,077 B2
(45) Date of Patent: May 3, 2005

(54) IMPLANTABLE CARDIAC STIMULATION DEVICE THAT DEFIBRILLATES THE ATRIA WHILE AVOIDING THE VENTRICULAR VULNERABLE PERIOD AND METHOD

(75) Inventors: Gene A. Bornzin, Simi Valley, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 471 days.

(21) Appl. No.: 10/086,580

(22) Filed: Feb. 28, 2002

(65) Prior Publication Data

US 2003/0163165 A1 Aug. 28, 2003

(51) Int. Cl.[7] .............................................. A61N 1/39
(52) U.S. Cl. ............................................. 607/4; 607/63
(58) Field of Search .............................. 607/4, 5, 9, 28, 607/63

(56) References Cited

U.S. PATENT DOCUMENTS

| | | | |
|---|---|---|---|
| 5,207,219 A | 5/1993 | Adams et al. | 128/419 D |
| 5,269,298 A | 12/1993 | Adams et al. | 128/419 D |
| 5,279,291 A | 1/1994 | Adams et al. | 607/5 |
| 5,282,836 A | 2/1994 | Kreyenhagen et al. | 607/4 |
| 5,350,402 A | 9/1994 | Infinger et al. | 607/5 |
| 5,391,185 A | 2/1995 | Kroll | 607/4 |
| 5,403,354 A | 4/1995 | Adams et al. | 607/5 |
| 5,411,524 A | 5/1995 | Rahul | 607/4 |
| 5,562,709 A | 10/1996 | White | 607/5 |
| 5,584,864 A | * 12/1996 | White | 607/5 |
| 5,683,429 A | 11/1997 | Mehra | 602/14 |
| 5,713,929 A | 2/1998 | Hess et al. | 607/14 |
| 5,713,932 A | 2/1998 | Gillberg et al. | 607/27 |
| 5,776,164 A | 7/1998 | Ripart | 607/5 |
| 5,810,739 A | 9/1998 | Bornzin et al. | 600/510 |
| 5,814,079 A | 9/1998 | Kieval | 607/4 |
| 5,836,976 A | 11/1998 | Min et al. | 607/6 |
| 5,954,752 A | 9/1999 | Mongeon et al. | 607/6 |
| 5,978,709 A | 11/1999 | Begemann et al. | 607/14 |
| 5,999,850 A | 12/1999 | Dawson et al. | 607/4 |
| 6,058,328 A | 5/2000 | Levine et al. | 607/14 |
| 6,081,745 A | 6/2000 | Mehra | 607/4 |
| 6,246,906 B1 | 6/2001 | Hsu et al. | 607/4 |

* cited by examiner

Primary Examiner—Kennedy Schaetzle

(57) ABSTRACT

An implantable cardiac stimulation device applies defibrillating electrical energy to the atria of a heart at a time which avoids inducing ventricular fibrillation of the heart. The device includes an atrial fibrillation detector that detects atrial fibrillation of the heart, a pacing pulse generator that applies a ventricular pacing pulse to the heart responsive to detection of atrial fibrillation, a timer that times a time period through an evoked response and a T-wave caused by the pacing pulse, and a defibrillation pulse generator that applies defibrillating electrical energy to the atria of the heart after the timer completes the timing of the time period.

61 Claims, 4 Drawing Sheets

IMPLANTABLE CARDIAC STIMULATION DEVICE THAT DEFIBRILLATES THE ATRIA WHILE AVOIDING THE VENTRICULAR VULNERABLE PERIOD AND METHOD

FIELD OF THE INVENTION

The present invention generally relates to an implantable cardiac stimulation device. The invention more particularly relates to such device and method for defibrillating the atria of a heart while avoiding the ventricular vulnerable period of the heart.

BACKGROUND OF THE INVENTION

Atrial fibrillation is a common cardiac arrhythmia. Although it is not life threatening, it is associated with strokes thought to be caused by blood clots forming in areas of stagnant blood flow as a result of prolonged atrial fibrillation. Symptoms of atrial fibrillation may include heart palpitations, dizziness, and even loss of consciousness.

Atrial fibrillation can occur suddenly. It is caused by chaotic activity of the atria of the heart. The chaotic atrial activity in turn causes the ventricular activity to be disassociated from the atrial activity. The ventricular activity becomes rapid and variable.

To terminate atrial fibrillation, it is often necessary to defibrillate the atria. This entails the delivery to the heart of a brief electrical shock. The shock may be applied externally through two electrodes placed on the chest or directly by an implantable device through implanted electrodes.

When atrial fibrillation is terminated by an electrical shock, it is most desirable to deliver the shock at a time which avoids the vulnerable period of the ventricles. The vulnerable period is that time within a cardiac cycle wherein myocardial tissue is prone to develop tachycardia or fibrillation when stimulated, even with a low magnitude electrical pulse. The vulnerable period of the ventricle is approximately represented on an electrocardiogram by the top of the T-wave. The T-wave represents the time in which the ventricular myocardium repolarizes following a ventricular depolarization (R-wave). To be safe, it is generally considered prudent to not deliver any shock to the heart during a T-wave.

The key then to defibrillating the atria is to avoid the T-wave of the ventricles. However, avoidance of the T-wave requires that the time of the T-wave be accurately known. This is difficult in the atrial fibrillation environment where the ventricular activity is erratic. During atrial fibrillation, the ventricular rate is generally elevated and irregular. Hence, predicting with any certainty as to when a T-wave will begin or end in an effort to safely terminate atrial fibrillation with a defibrillating shock would be clinically impossible.

SUMMARY OF THE INVENTION

The present invention provides an implantable cardiac stimulation device that applies defibrillating electrical energy to the atria of a heart and at a time which avoids the ventricular vulnerable period. More particularly, the device, after detecting atrial fibrillation, applies a ventricular pacing pulse to the heart to cause a ventricular evoked response. This results in a following T-wave. Since the evoked response results from a pacing pulse, the occurrence and duration of the resulting T-wave may be predicted to permit an atrial defibrillating pulse to be applied after the T-wave to defibrillate the heart during a time which is known not to be a ventricular vulnerable period.

Hence, the present invention provides an implantable cardiac stimulation device that applies defibrillating electrical energy to atria of a heart at a time which avoids inducing ventricular fibrillation of the heart. The device includes an atrial fibrillation detector that detects atrial fibrillation of the heart, a pacing pulse generator that applies a pacing pulse to at least one of the ventricles responsive to the atrial fibrillation detector detecting atrial fibrillation of the heart, a timer that times a time period through an evoked response, and a T-wave caused by the pacing pulse, the time period completing after the T-wave and before an immediately following R-wave, and a defibrillation pulse generator that applies the defibrillating electrical energy to the atria of the heart responsive to the timer completing the timing of the time period.

The present invention further provides an implantable cardiac stimulation device for applying defibrillating electrical energy to atria of a heart at a time which avoids inducing ventricular fibrillation of the heart. The device includes atrial fibrillation detecting means for detecting atrial fibrillation of the heart and ventricular pacing pulse generating means for applying a pacing pulse to at least one of the ventricles responsive to the detection of atrial fibrillation. The device further includes timing means for timing a time period through an evoked response and T-wave caused by the ventricular pacing pulse and the fibrillation pulse generating means for applying defibrillating electrical energy to the atria after the timing means times the time period.

The present invention still further provides a method of applying defibrillating electrical energy to atria of a heart at a time which avoids inducing ventricular fibrillation of the heart in an implantable cardiac stimulation device. The method includes the steps of detecting for atrial fibrillation of the heart, stimulating at least one of the ventricles with a ventricular pacing pulse responsive to the detection of atrial fibrillation, timing a time period through an evoked response and T-wave caused by the ventricular pacing pulse, and applying defibrillating electrical energy to the atria after timing the time period.

Before applying the atrial defibrillation shock, the pacing pulse generator may apply a plurality of pacing pulses to at least one of the ventricles responsive to the atrial fibrillation detector detecting atrial fibrillation of the heart. The timer may time the time period following a last one of the plurality of pacing pulses through the evoked response and T-wave caused by the last one of the plurality of pacing pulses. The pacing pulse generator preferably applies the plurality of pacing pulses on demand and the timer times the time period after the pacing pulse generator applies the plurality of pacing pulses during consecutive cardiac cycles.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
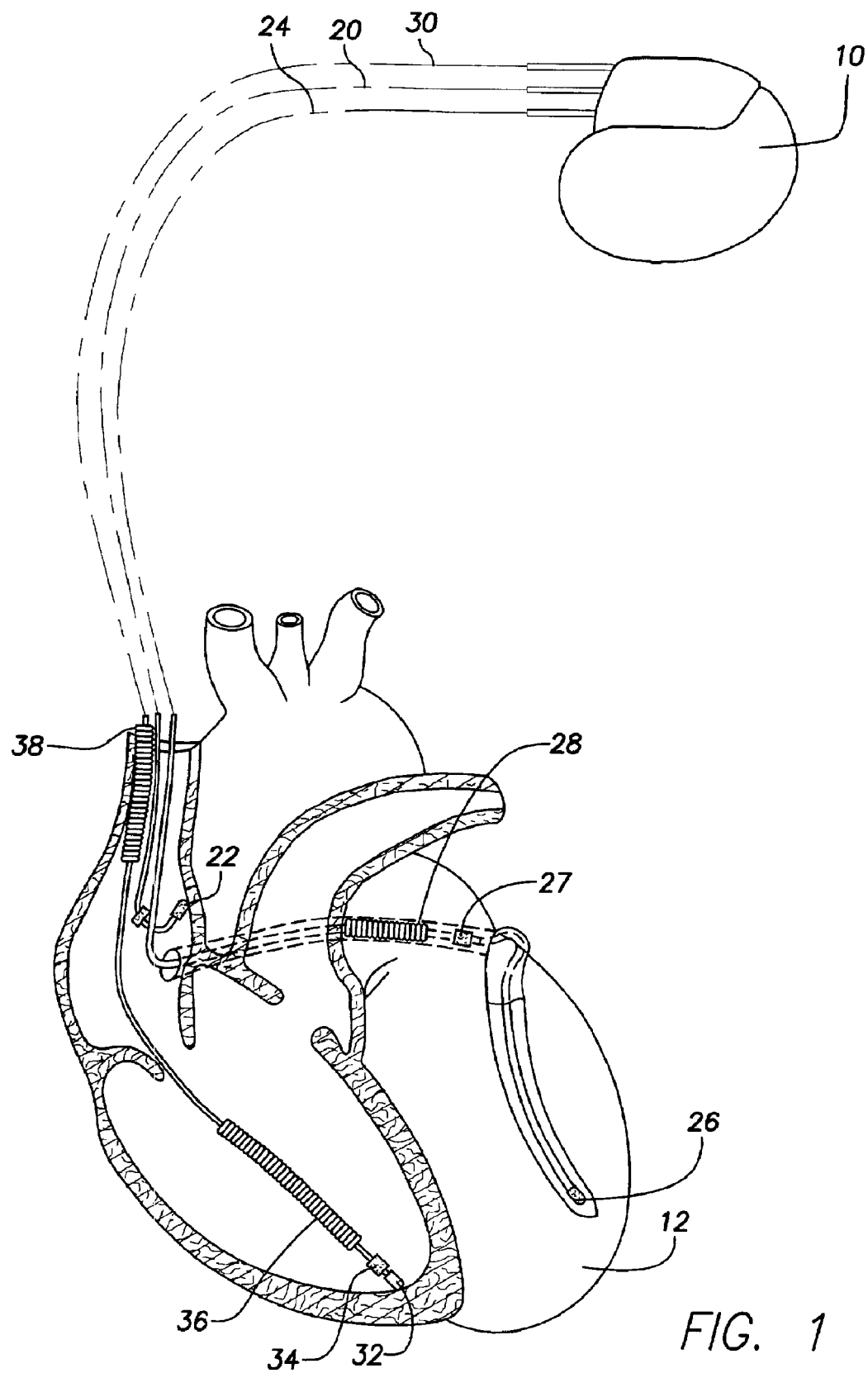
FIG. 1 is a simplified diagram illustrating an implantable cardiac stimulation device embodying the present invention in electrical communication with at least three leads implanted in a patient's heart and which is capable of delivering multi-chamber stimulation and shock therapy including atrial defibrillation therapy in accordance with the present invention.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

As will be described subsequently, the coil electrodes 28 and 38 may be employed for defibrillating the atria. This electrode configuration is most advantageous for atrial defibrillation because it directs the electrical energy primarily through atrial myocardium.

Figure 2:
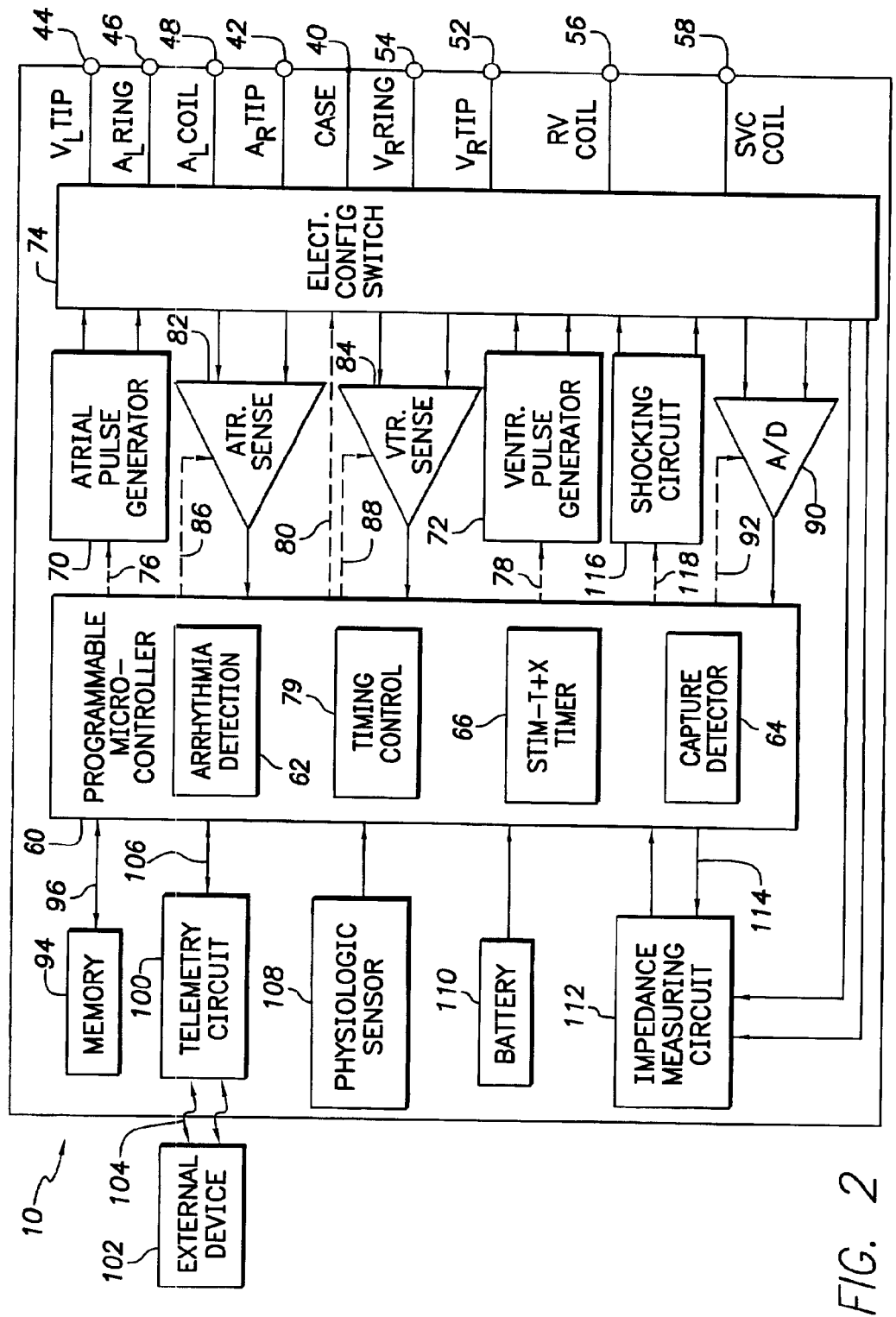
FIG. 2 is a functional block diagram of the multi-chamber implantable stimulation device of FIG. 1 illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of cardiac intervals, refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, including atrial fibrillation detection, the device 10 includes an arrhythmia detector 62 which utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller further includes a capture detector 64. Advantageously, the data acquisition system 90 may be coupled to the microcontroller to support detection of evoked responses from the heart 12 in response to applied stimuli. Capture occurs when an electrical stimulus applied to the heart depolarizes the cardiac tissue, thereby causing the heart muscle to contract. The capture detector 64 of the microcontroller 60 may detect a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window. Based on the amplitude of the signal within the capture detection window, the capture detector 64 determines if capture has occurred. As will be seen subsequently, evoked response detection may be used as a prerequisite to atrial defibrillation.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). As further noted above, the electrode configuration of the coil electrodes 38 and 28 is particularly advantageous for defibrillating the atria of the heart.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules). For ventricular defibrillation, the shocks may be delivered asynchronously (since R-waves may be too disorganized). For atrial defibrillation, shock delivery is preferably timed in accordance with the present invention as described, for example, in connection with the preferred embodiment herein.

The microcontroller 60 further includes another timer 66. Timer 66 may be employed in accordance with the present invention to time a time period which extends through a ventricular evoked response and resulting T-wave. The timer 66 may extend the timing by X milliseconds, for example, 100 milliseconds.

Figure 3:
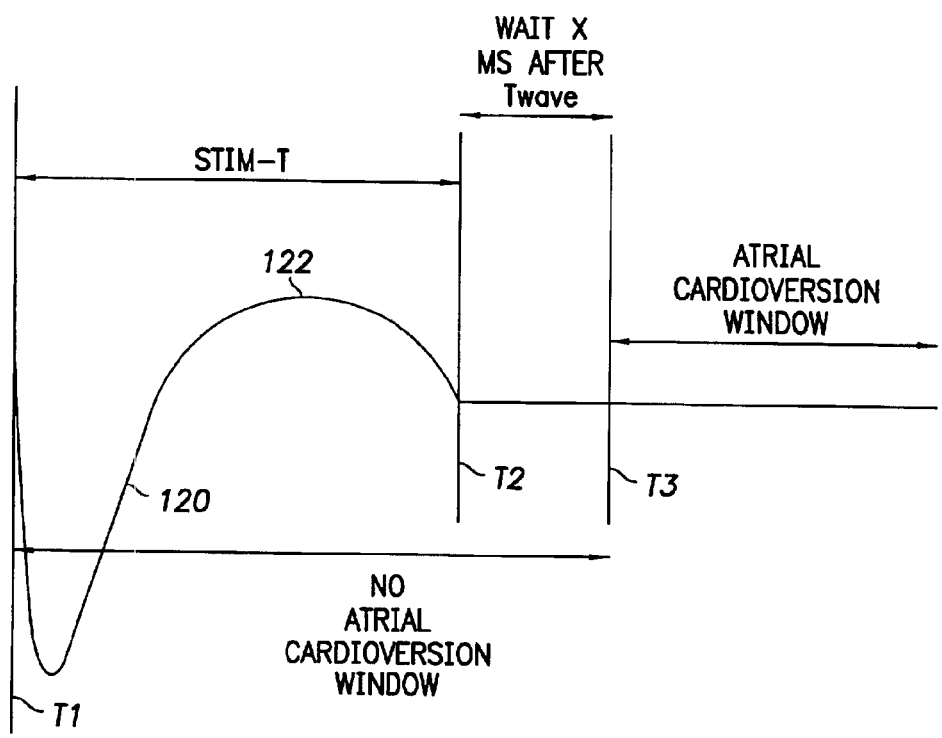
FIG. 3 is a ventricular electrocardiogram illustrating a ventricular evoked response and T-wave to lend better understanding of the preferred embodiment of the present invention.

The purpose of the timer 66 will now be generally described with reference to the electrocardiogram of FIG. 3. After the arrhythmia detector 62 detects atrial fibrillation, the atria are defibrillated. The timing of the atrial fibrillation is controlled by the timer 66.

More specifically, once atrial fibrillation is detected, a pacing pulse is applied to either one or both of the ventricles at time T1. This causes the timer 66 to commence timing. The timer 66 times through the resulting evoked response 120 and the resulting T-wave 122. The T-wave completes (the ventricular myocardium is fully repolarized) at time T2 after a time period of STIM-T. This begins a time window beyond the ventricular vulnerable period where the atria may be defibrillated safely without inducing ventricular fibrillation. In accordance with this embodiment, the timer 66 continues to time for an additional X milliseconds to time T3 where X may be, for example, 100 milliseconds. The additional time of X milliseconds may be provided to assure that the ventricular vulnerable period has passed. The atria may now, after time T3, be defibrillated with the application of electrical energy by the shocking circuit 116 across the coil electrodes 28 and 33. The atrial cardioversion/defibrillation window remains open until the next intrinsic ventricular activation (R-wave) is sensed.

As a condition for atrial defibrillation, the capture detector 64 may be required to actually detect the evoked response. This confirmation will confirm the presence of the T-wave 122 and assure proper timing of the electrical shock relative to the T-wave 122. If the capture detector 64 fails to detect the evoked response 120, the delivery of the atrial defibrillation/cardioversion shock may be aborted.

Figure 4:
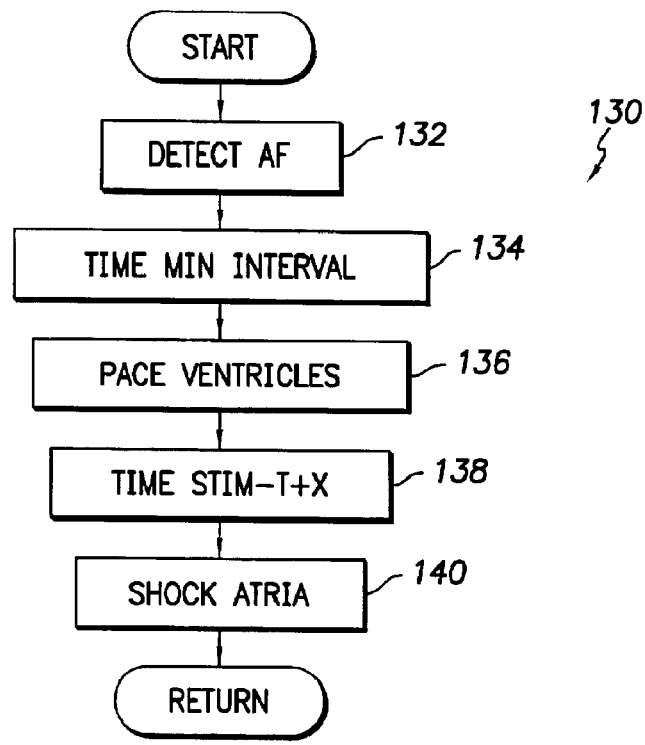
FIG. 4 is a flow chart describing an overview of the operation of one embodiment of the present invention.

In FIG. 4, a flow chart is shown describing an overview of the operation and particular novel features implemented in one embodiment of the device 10. In this flow chart, and the flow chart of FIG. 5 to be described subsequently, the various algorithmic steps are summarized in individual "blocks". Such blocks describe specific actions or decisions that must be made or carried out as the algorithm proceeds. Where a microcontroller (or equivalent) is employed, the flow chart provided herein provides the basis for a "control program" that may be used by such a microcontroller (or equivalent) to effectuate the desired control of the stimulation device. Those skilled in the art may readily write such a control program based on the flow chart and other descriptions presented herein.

The method illustrated in the flow chart 130 of FIG. 4 initiates at an activity block 132. In activity block 132 atrial fibrillation is detected. The atrial fibrillation episode may be detected as previously described herein or in accordance with other methods well known in the art. Once atrial fibrillation is detected in accordance with activity block 132, the process advances to activity block 134 wherein the timing control 79 times a cardiac interval having a length greater than a minimum interval. The minimum interval may be, for example, 500 milliseconds or greater. Detection of such a minimum interval prior to the application of the atrial therapy may be desirable to assure that the cardiac rate is acceptable for accurate vulnerable period timing.

Once the minimum cardiac interval has been timed, the process advances to activity block 136 wherein either one or both of the ventricles is paced. Here, the ventricular pulse generator 72 applies a pacing pulse to one of the right and left ventricles, or to both the right ventricle and left ventricle simultaneously. Upon the pacing of the ventricles in accordance with activity block 136, the process then advances to activity block 138 wherein the timer 66 begins timing the STIM-T+X time period as previously described with reference to FIG. 3. Again, as previously mentioned, the additional timing period of X milliseconds may be, for example, 100 milliseconds.

After the STIM-T+X time period has been timed, the atrial defibrillating/cardioverting electrical shock may be applied across the electrodes 28 and 38 in accordance with activity block 140. The electrical energy used to cardiovert/defibrillate the atria may have a magnitude of, for example, 5 joules and a biphasic waveform of the type well known in the art. Of course, those skilled in the art will appreciate that the magnitude of the electrical energy may vary from patient to patient and atrial defibrillation/cardioversion electrode configurations. Once the atria have been defibrillated in accordance with activity block 140, the process returns for the detection of the next atrial fibrillation episode.

The atrial therapy described with reference to FIG. 4 may include additional process steps if desired. For example, the delivery of the atrial defibrillating/cardioverting shock may be made dependent upon the detection of the evoked response 122 (FIG. 3) as previously described with reference to FIG. 3. Additionally, the electrical energy delivered to the atrial may be further timed off of atrial activity, such as a P-wave. To that end, the atrial sensing circuit 82 may be utilized for sensing a P-wave during the atrial cardioversion/defibrillation window commencing after time T3 from which the atrial defibrillating electrical energy may be timed. The atria may be defibrillated/cardioverted at any time during this period up to the sensing of the next intrinsic ventricular activation (R-wave).

As a further additional method step to the method described with reference to FIG. 4, the atrial defibrillating/cardioverting electrical energy may be applied after an atrial pacing pulse is applied to the atria. Here, once the timer 66 has timed the STIM-T+X time period, the atrial pulse generator 70 may issue a pacing pulse to either one or both of the atria. The delivery of the atrial defibrillating/cardioverting electrical energy may then be timed off from the atrial pacing pulse until the sensing of the next R-wave. The initial pacing of the atria prior to the application of the atrial defibrillating/cardioverting energy may be desirable because it may assist in synchronizing more of the atrial tissue and potentially allow atrial cardioversion/defibrillation at relatively low electrical energies.

The present invention provides a method of defibrillating/cardioverting the atria which has a number of advantages. First, the method in accordance with the present invention requires only one ventricular paced event to trigger atrial cardioversion/defibrillation. Further, the pacing of the ventricles provides an opportunity to detect the evoked response to confirm the presence of the T-wave and accuracy in the timing through the evoked response and T-wave to avoid the ventricular vulnerable period. Another advantage is that the method of the present invention provides more freedom in timing the atrial cardioversion. Once the timer 66 has timed through the T-wave, the atria may be cardioverted/defibrillated at any time up to the next sensed R-wave. Still further, the elective pacing of the atria prior to atrial cardioversion may reduce the energy required in cardioverting/defibrillating the atria. Alternatively, the atrial cardioverting/defibrillating electrical energy may be delivered at a time synchronized to a spontaneous atrial depolarization. As a result, the atrial defibrillation/cardioversion therapy contemplated by the present invention allows for the delivery of the defibrillating/cardioverting electrical energy to the atria at a time which is assured to be safe against the induction of ventricular fibrillation.

Figure 5:
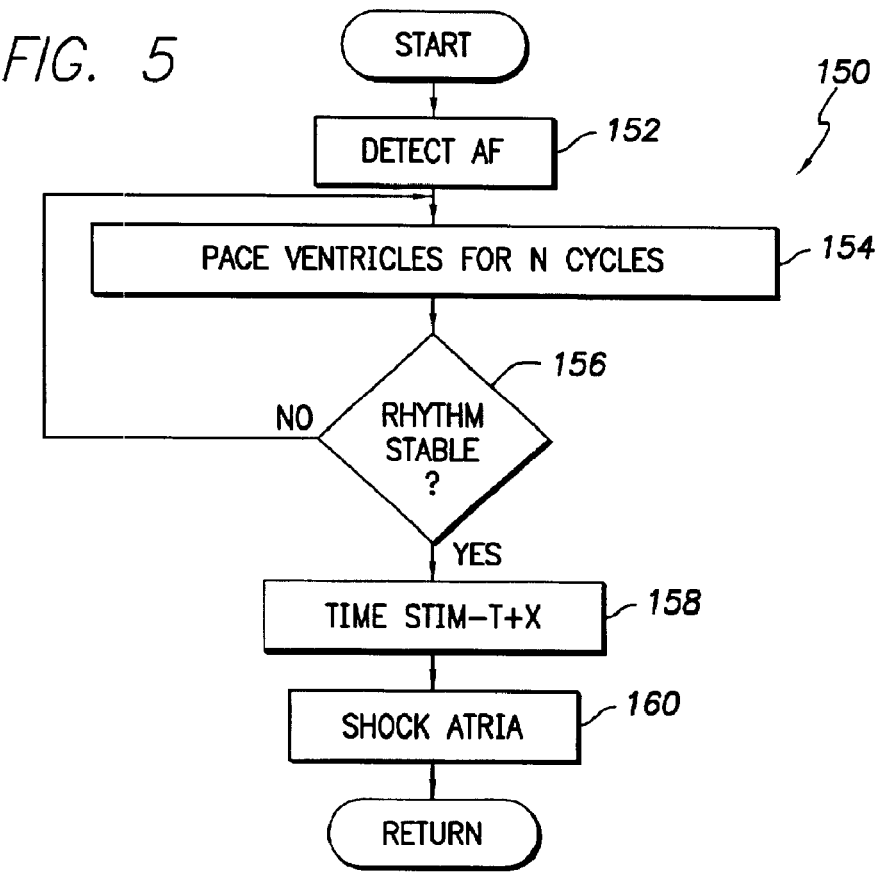
FIG. 5 is a flow chart describing an overview of the operation of another embodiment of the present invention.

In FIG. 5, a flow chart is shown describing an overview of the operation and particular novel features implemented in a second embodiment of the device 10. In accordance with this embodiment, a series of ventricular pacing pulses is delivered at a programmable rate (e.g. 90 bpm). This will have the beneficial effect of stabilizing the ventricular rate by a phenomenon known as retrograde concealed conduction thus effectively eliminating potential long-short cycle sequences that may predispose to the adverse induction of ventricular tachyarrhythmias in response to a shock delivered to convert atrial fibrillation. The method illustrated in the flow chart 150 of FIG. 5 initiates at an activity block 152. In activity block 152 atrial fibrillation is detected. The atrial fibrillation episode may be detected as previously described herein or in accordance with other methods well known in the art. Once atrial fibrillation is detected in accordance with activity block 152, the process advances to activity block 154 wherein ventricular pacing is initiated at a programmable rate (e.g. 90 bpm) for a preset number of N cycles. Here, the ventricular pulse generator 72 applies pacing pulses to one of the right and left ventricles, or to both the right ventricle and left ventricle simultaneously. Preferably the pacing is performed on demand. With the $N^{th}$ ventricular pacing pulse, the process advances to decision block 156. Here it is determined if the rhythm is stable. If the rhythm is stable, then the algorithm proceeds to block 158. If the rhythm is not stable as exemplified by multiple native ventricular beats interspersed within the ventricular paced rhythm, the process returns to block 154 and reinstates ventricular pacing while withholding shock therapy.

Once a stable paced cardiac interval has been determined in decision block 156, the process advances to activity block 158 wherein the timer 66 times the STIM-T+X time period as previously described with reference to FIG. 3. Preferably, the timer 66 is started with the delivery of the $N^{th}$ pacing pulse. N may be, for example, eight or more pacing pulses and again, as previously mentioned, the additional timing period of X milliseconds may be, for example, 100 milliseconds.

After the STIM-T+X time period has been timed, the atrial defibrillating/cardioverting electrical shock may be applied across the electrodes 28 and 38 in accordance with activity block 160. The electrical energy used to cardiovert/defibrillate the atria may have a magnitude of, for example, 5 joules and a biphasic waveform of the type well known in the art. Of course, those skilled in the art will appreciate that the magnitude of the electrical energy may vary from patient to patient and atrial defibrillation/cardioversion electrode configurations. Once the atria have been defibrillated in accordance with activity block 140, the process returns for the detection of the next atrial fibrillation episode.

The atrial therapy described with reference to FIG. 5 may include additional process steps if desired. For example, following detecting of atrial fibrillation, the timing control 79 may time a cardiac interval having a length greater than a minimum interval of, for example, 500 milliseconds or greater. This may be desirable to assure accurate vulnerable period timing and success in being able to establish a stable rhythm through the ventricular pacing. Further, the delivery of the atrial defibrillating/cardioverting shock may be made dependent upon the detection of the ventricular evoked response 122 (FIG. 3) as previously described with reference to FIG. 3. Additionally, the electrical energy delivered to the atria may be further timed off of atrial activity, such as a Fibrillatory-wave. To that end, the atrial sensing circuit 82 may be utilized for sensing a Fibrillation-wave during the atrial cardioversion/defibrillation window commencing after time T3 (FIG. 3) from which the atrial defibrillating electrical energy may be timed. The atrial may be defibrillated/cardioverted at any time during this period up to the sensing of the next intrinsic ventricular activation (R-wave).

As a further additional method step to the method described with reference to FIG. 5, the atrial defibrillating/cardioverting electrical energy may be applied after an atrial pacing pulse is applied to the atria. Here, once the timer 66 has timed the STIM-T+X time period, the atrial pulse generator 70 may issue a pacing pulse to either one or both of the atria. The delivery of the atrial defibrillating/ cardioverting electrical energy may then be timed off from the atrial pacing pulse until the sensing of the next R-wave. The initial pacing of the atria prior to the application of the atrial defibrillating/cardioverting energy may be desirable because it may assist in synchronizing more of the atrial tissue and potentially allow atrial cardioversion/ defibrillation at relatively low electrical energies.

The present invention provides a method of defibrillating/ cardioverting the atria which has a number of advantages. First, the method in accordance with the present invention requires only one ventricular paced event to trigger atrial cardioversion/defibrillation. Further, the pacing of the ventricles provides an opportunity to detect the evoked response to confirm the presence of the T-wave and accuracy in the timing through the evoked response and T-wave to avoid the ventricular vulnerable period. Another advantage is that the method of the present invention provides more freedom in timing the atrial cardioversion. In the second embodiment, a period of ventricular pacing is provided to stabilize the ventricular rhythm and eliminate long-short cycle sequences further improving the safety of the shock by reducing the chance of inducing ventricular fibrillation. Once the timer 66 has timed through the T-wave, the atria may be cardioverted/ defibrillated at any time up to the next sensed R-wave. Still further, the elective pacing of the atria prior to atrial cardioversion may reduce the energy required in cardioverting/ defibrillating the atria. Alternatively, the atrial cardioverting/ defibrillating electrical energy may be delivered at a time synchronized to a spontaneous atrial depolarization. As a result, the atrial defibrillation/cardioversion therapy contemplated by the present invention allows for the delivery of the defibrillating/cardioverting electrical energy to the atria at a time which is assured to be safe against the induction of ventricular fibrillation.

While the invention has been described by means of specific embodiments and applications thereof, it is understood that numerous modifications and variations could be made thereto by those skilled in the art without departing from the spirit and scope of the invention. For instance, the disclosed features, either singularly or in groups, could be used with other leads to advantageous results. It is therefore to be understood that within the scope of the claims, the invention may be practiced otherwise than as specifically described herein.

What is claimed is:

1. An implantable cardiac stimulation device that applies defibrillating electrical energy to at least one atrium of a heart at a time which avoids inducing ventricular fibrillation of the heart, the device comprising:

an atrial fibrillation detector that detects atrial fibrillation of the heart;

a pacing pulse generator that applies a pacing pulse to at least one of the ventricles responsive to the atrial fibrillation detector detecting atrial fibrillation of the heart;

a timer that times a time period through an evoked response end a T-wave caused by the pacing pulse, the time period completing a predetermined time period after the T-wave ends; and a defibrillation pulse generator that applies the defibrillating eletrical energy to the at least one atrium of the heart responsive to the timer completing the timing of the time period.

2. The device of claim 1 wherein the timer commences timing of the time period beginning with the application of the pacing pulse.

3. The device of claim 2 wherein the time period is between about 350 milliseconds and 450 milliseconds.

4. The device of claim 1 wherein the pacing pulse generator applies the pacing pulse to the right ventricle of the heart.

5. The device of claim 1 wherein the pacing pulse generator applies the pacing pulse to the left ventricle of the heart.

6. The device of claim 1 wherein the pacing pulse generator applies the pacing pulse to both the right ventricle and the left ventricle of the heart.

7. The device of claim 1 further comprising a cardiac interval timer that times cardiac intervals of the heart responsive to the atrial fibrillation detector detecting atriel fibrillation of the heart and wherein the pacing pulse generator applies the pacing pulse after the interval timer times a cardiac interval longer than a minimum cardiac interval.

8. The device of claim 1 further comprising an evoked response detector that detects the evoked response and wherein the defibrillation pulse generator inhibits the application of the defibrillating energy responsive to the evoked response detector failing to detect the evoked response.

9. The device of claim 1 wherein the pacing pulse generator applies a plurality of pacing pulses to at least one of the ventricles responsive to the atrial fibrillation detector detecting atrial fibrillation of the heart, and wherein the timer times the time period following a last one of the plurality of pacing pulses through the evoked response and T-wave caused by the last one of the plurality of pacing pulses.

10. The device of claim 9 wherein the pacing pulse generator applies the plurality of pacing pulses on demand and wherein the timer times the time period after the pacing pulse generator applies the plurality of pacing pulses during consecutive cardiac cycles.

11. The device of claim 9 wherein the timer commences timing of the time period beginning with the application of the last one of the pacing pulses.

12. The device of claim 11 wherein the time period is between about 350 milliseconds and 450 milliseconds.

13. The device of claim 9 wherein the pacing pulse generator applies the pacing pulses to the right ventricle of the heart.

14. The device of claim 9 wherein the pacing pulse generator applies the pacing pulses to the left ventricle of the heart.

15. The device of claim 9 wherein the pacing pulse generator applies the pacing pulses to both the right ventricle and the left ventricle of the heart.

16. The device of claim 9 further comprising an evoked response detector that detects the evoked response and wherein the defibrillation pulse generator inhibits the application of the defibrillating energy responsive to the evoked response detector failing to detect the evoked response.

17. The device of claim 9 further comprising an atrial pacing pulse generator that applies an atrial pacing pulse to at least one of the atria after the timer completes the timing of the time period and before the defibrillation pulse generator applies the defibrillating electrical energy to the atria.

18. The device of claim 9 further comprising an atrial sensing circuit that senses P-waves of the heart and wherein the defibrillation pulse generator applies the defibrillating electrical energy to the atria in timed relation to a sensed P-wave.

19. An implantable cardiac stimulation device that applies defibrillating electrical energy to at least one atrium of a heart at a time which avoids inducing ventricular fibrillation of the heart, the device comprising:
- an atrial fibrillation detector that detects atrial fibrillation of the heart;
- a pacing pulse generator that applies a pacing pulse to at least one of the ventricles responsive to the atrial fibrillation detector detecting atrial fibrillation of the heart;
- a timer that times a time period through an evoked response and a T-wave caused by the pacing pulse, the time period completing after the T-wave;
- a defibrillation pulse generator that applies the defibrillating electrical energy to the at least one atrium of the heart responsive to the timer completing the timing of the time period; and
- an atrial pacing pulse generator that applies an atrial pacing pulse to at least one of the atria after the timer completes the timing of the time period and before the defibrillation pulse generator applies the defibrillating electrical energy to the atria.

20. An implantable cardiac stimulation device that applies defibrillating electrical energy to at least one atrium of a heart at a time which avoids inducing ventricular fibrillation of the heart, the device comprising:
- an atrial fibrillation detector that detects atrial fibrillation of the heart;
- a pacing pulse generator that applies a pacing pulse to at least one of the ventricles responsive to the atrial fibrillation detector detecting atrial fibrillation of the heart;
- a timer that times a time period through an evoked resoonse and a T-wave caused by the pacing pulse, the time period completing after the T-wave;
- a defibrillation pulse generator that applies the defibrillating electrical energy to the at least one atrium of the heart responsive to the timer completing the timing of the time period; and
- an atrial sensing circuit that senses P-waves of the heart and wherein the defibrillation pulse generator applies the defibrillating electrical energy to the atria in timed relation to a sensed P-wave.

21. An implantable cardiac stimulation device for applying defibrillating electrical energy to at least one atrium of a heart at a time which avoids inducing ventricular fibrillation of the heart, the device comprising:
- atrial fibrillation detecting means for detecting atrial fibrillation of the heart;
- ventricular pacing pulse generating means for applying a pacing pulse to at least one of the ventricles responsive to the detection of atrial fibrillation;
- timing means for timing a time period through an evoked response and T-wave caused by the ventricular pacing pulse and ending a predetermined time period after the T-wave ends; and
- defibrillation pulse generating means for applying defibrillating electrical energy to the atria after the timing means times the time period.

22. The device of claim 21 wherein the timing means commences timing of the time period beginning with the application of the pacing pulse.

23. The device of claim 22 wherein the time period is between about 350 milliseconds and 450 milliseconds.

24. The device of claim 21 wherein the pacing pulse generating means applies the pacing pulse to the right ventricle of the heart.

25. The device of claim 21 wherein the pacing pulse generating means applies the pacing pulse to the left ventricle of the heart.

26. The device of claim 21 wherein the pacing pulse generating means applies the pacing pulse to both the right ventricle and the left ventricle of the heart.

27. The device of claim 21 further comprising cardiac interval timing means for timing cardiac intervals of the heart responsive to the atrial fibrillation detector means detecting atrial fibrillation of the heart and wherein the pacing pulse generating means applies the pacing pulse after the interval timing means times a cardiac interval longer than a minimum cardiac interval.

28. The device of claim 21 further comprising evoked response detecting means for detecting the evoked response and wherein the defibrlliation pulse generating means wtthholds the application of the defibrillating energy responsive to the evoked response detecting means failing to detect the evoked response.

29. The device of claim 21 wherein the ventricular pacing pulse generating means applies a plurality of pacing pulses to at least one of the ventricles responsive to the detection of atrial fibrillation, and wherein the timing means times the time period following a last one of the plurality of pacing pulses through the evoked response and T-wave caused by the last one of the plurality of pacing pulses.

30. The device of claim 29 wherein the ventricular pacing pulse generating means applies the plurality of pacing pulses on demand and wherein the timing means times the time period after the ventricular pacing pulse generating means applies the plurality of pacing pulses during consecutive cardiac cycles.

31. The device of claim 29 wherein the timing means commences timing of the time period beginning with the application of the last one of the pacing pulses.

32. The device of claim 31 wherein the time period is between about 350 milliseconds and 450 milliseconds.

33. The device of claim 29 wherein the pacing pulse generating means applies the pacing pulses to the right ventricle of the heart.

34. The device of claim 29 wherein the pacing pulse generating means applies the pacing pulses to the left ventricle of the heart.

35. The device of claim 29 wherein the pacing pulse generating means applies the pacing pulses to both the right ventricle and the left ventricle of the heart.

36. The device of claim 29 further comprising evoked response detecting means for detecting the evoked response and wherein the defibrillation pulse generating means withholds the application of the defibriliating energy responsive to the evoked response detecting means failing to detect the evoked response.

37. The device of claim 29 further comprising atrial pacing pulse generating means for applying an atrial pacing pulse to at least one of the atrial after the timing means times the time period and before the defibrillation pulse generating means applies the defibrillating electrical energy to the atria.

38. The device of claim 29 further comprising atrial sensing means for sensing P-waves of the heart and wherein the defibrillation pulse generating means applies the defibrillating electrical energy to the atria in timed relation to a sensed P-wave.

39. An implantable cardiac stimulation device for applying defibrillating electrical energy to at least one atrium of a heart at a time which avoids inducing ventricular fibrillation of the heart, the device comprising:
- atrial fibrillation detecting means for detecting atrial fibrillation of the heart;

ventricular pacing pulse generating means for applying a first pacing pulse to at least one of the ventricles responsive to the detection of atrial fibrillation;

timing means for timing a time period through an evoked response and T-wave caused by the ventricular pacing pulse;

defibrillation pulse generating means for applying defibrillating electrical energy to the atria after the timing means times the time period; and atrial pacing pulse generating means for applying an atrial pacing pulse to at least one of the atria after the timing means times the time period and before the defibrillation pulse generating means applies the defibrillating eletrical energy to the atria.

40. An implantable cardiac stimulation device for appying defibriliating electrical energy to at least one atrium of a heart at a time which avoids inducing ventricular fibrillation of the heart, the device comprising:

atrial fibrillation detecting means for detecting atrial fibrillation of the heart;

ventricular pacing pulse generating means for applying a first pacing pulse to at least one of the ventricles responsive to the detection of atrial fibrillation;

timing means for timing a time period through an evoked response and T-wave caused by the ventricular pacing pulse;

defibrillation pulse generating means for applying defibrillating electrical energy to the atria after the timing means times the time period; and atrial sensing means for sensing P-waves of the heart and wherein the defibrillation pulse generating means applies the defibrillating electrical energy to the atria in timed relation to a sensed P-wave.

41. In an implantable cardiac stimulation device, a method of applying defibrillating electrical energy to at least one atrium of a heart, the method comprising:

stimulating at least one of the ventricles with a ventricular pacing pulse to cause an evoked response and T-wave;

waiting until the T-wave ends; and applying defibrillating electrical energy to the at least one atrium a predetermined period after the T-wave ends.

42. The method of claim 41 wherein waiting comprises commencing timing of a predetermined time period beginning with the application of the pacing pulse.

43. The method of claim 42 wherein the time period is between about 350 milliseconds and 450 milliseconds.

44. The method of claim 41 wherein stimulating comprises applying the pacing pulse to the right ventricle of the heart.

45. The device of claim 41 further comprising detecting the evoked response including the T-wave and wherein applying is performed after the detected T-wave ends.

46. The method of claim 41 wherein stimulating comprises applying the pacing pulse to both the right ventricle and the left ventricle of the heart.

47. The method of claim 41 further comprising timing cardiac intervals of the heart responsive to detecting atrial fibrillation of the heart and wherein stimulating is performed after the timing of a cardiac interval longer than a minimum cardiac interval.

48. The method of claim 41 further comprising detecting the evoked response and wherein applying is performed only when the evoked response is detected.

49. The method of claim 41 wherein stimulating comprises applying a plurality of pacing pulses to at least one of the ventricles responsive to the detection of atrial fibrillation, and wherein timing comprises timing the time period following a last one of the plurality of pacing pulses through the evoked response end T-wave caused by the last one of the plurality of pacing pulses.

50. The method of claim 49 wherein stimulating comprises applying the plurality of pacing pulses on demand and wherein timing is commenced after the plurality of pacing pulses are applied during consecutive cardiac cycles.

51. The method of claim 49 wherein timing comprises commencing the timing of the time period beginning with the application of the last one of the pacing pulses.

52. The method of claim 51 wherein the time period is between about 350 milliseconds and 450 milliseconds.

53. The method of claim 49 wherein stimulating comprises applying the pacing pulse to the right ventricle of the heart.

54. The device of claim 49 wherein stimulating comprises applying the pacing pulses to the left ventricle of the heart.

55. The method of claim 49 wherein stimulating comprises applying the pacing pulses to both the right ventricle and the left ventricle of the heart.

56. The method of claim 49 further comprising detecting the evoked response and wherein applying is performed only when the evoked response is detected.

57. The method of claim 49 further comprising pacing at least one of the atria after the timing of the time period and before the applying of the defibrillating electrical energy to the atria.

58. The method of claim 49 further comprising sensing P-waves of the heart and wherein applying comprises applying the defibrillating electrical energy to the atria in timed relation to a sensed P-wave.

59. In an implantable cardiac stimulation device, a method of applying defibrillating electrical energy to at least one atrium of a heart, the method comprising:

stimulating at least one of the ventricles with a ventricular pacing pulse to cause an evoked response and T-wave;

waiting until the T-wave ends;

applying defibrillating electrical energy to the at least one atrium after the T-wave ends; and pacing at least one of the atria after the timing of the time period and before the applying of the defibrillating electrical energy to the atria.

60. In an implantable cardiac stimulation device, a method of applying defibrillating electrical energy to at least one atrium of a heart, the method comprising:

stimulating at least one of the ventricles with a ventricular pacing pulse to cause an evoked response and T-wave;

waiting until the T-wave ends;

applying defibrillating electrical energy to the at least one atrium after the T-wave ends; and sensing P-waves of the heart and wherein applying comprises applying the defibrillating electrical energy to the atria in timed relation to a sensed P-wave.

61. An implantable cardiac stimulation device comprising:

a lead assembly that is in electrical communication with a heart to sense physiologic activity of the heart and generate corresponding signals, and to deliver stimulation energy to the heart;

a pulse generator connected to the lead assembly and that generates stimulation pulses to be delivered to the heart via the lead assembly; and control circuitry connected to the lead assembly and pulse generator, the control circuitry being operative to process the signals from the lead assembly to determine whether atrial fibrillation exists, the control circuitry being operative in response to detection of atrial fibrillation to control the pulse generator to generate at least one pacing pulse for delivery to at least one ventricle to cause an evoked response and T-wave in the at least one ventricle, the control circuitry further being operative to control the pulse generator to generate a defibrillation pulse for delivery to at least one atrium a predetermined period after the T-wave ends.

* * * * *